United States Patent [19]

Mroczkowski et al.

[11] Patent Number: 4,794,089

[45] Date of Patent: Dec. 27, 1988

[54] METHOD FOR ELECTRONIC DETECTION OF A BINDING REACTION

[75] Inventors: Susan J. Mroczkowski, Franklin; Kenneth A. Siegesmund, Brookfield; Donald E. Yorde, Greenfield, all of Wis.

[73] Assignee: Midwest Research Microscopy, Inc., Milwaukee, Wis.

[21] Appl. No.: 843,982

[22] Filed: Mar. 25, 1986

[51] Int. Cl.$^4$ ............................................. G01N 33/53
[52] U.S. Cl. .................................... 436/501; 436/518; 436/531; 436/806; 436/807; 436/809; 204/403
[58] Field of Search ............... 436/501, 518, 531, 806, 436/807, 809; 204/403

[56] References Cited

U.S. PATENT DOCUMENTS

| | | |
|---|---|---|
| 3,074,853 | 1/1963 | Brewer . |
| 3,853,467 | 12/1974 | Giaever . |
| 3,926,564 | 12/1975 | Giaever . |
| 4,054,646 | 10/1977 | Giaver .............................. 436/806 |
| 4,072,576 | 2/1978 | Arwin et al. ..................... 436/806 |
| 4,157,323 | 6/1979 | Yen et al. . |
| 4,180,771 | 12/1979 | Guckel . |
| 4,191,739 | 3/1980 | Hzgiris . |
| 4,198,389 | 4/1980 | Wadsworth . |
| 4,206,094 | 6/1980 | Yen et al. . |
| 4,219,335 | 8/1980 | Ebersole ........................... 436/806 |
| 4,219,411 | 8/1980 | Yen et al. . |
| 4,225,410 | 9/1980 | Pace . |
| 4,233,144 | 11/1980 | Pace . |
| 4,238,757 | 12/1980 | Schenck ........................... 436/806 |
| 4,287,300 | 9/1981 | Gibbons . |
| 4,327,073 | 4/1982 | Huang . |
| 4,334,880 | 6/1982 | Malmros . |
| 4,399,099 | 8/1983 | Buckles . |
| 4,420,558 | 12/1983 | De Mey et al. . |
| 4,444,892 | 4/1984 | Malmros ........................... 436/528 |
| 4,446,238 | 5/1984 | De Mey et al. . |
| 4,459,360 | 7/1984 | Marinkovich . |

FOREIGN PATENT DOCUMENTS 0029658 2/1985 Japan ................................. 204/403
2080339 of 0000 United Kingdom .

OTHER PUBLICATIONS

The Journal of Histochemistry and Cytochemistry, *A Quantitative Immunoperoxidase Procedure Employing Energy Dispersive X-Ray Analysis.*
Derwent Abstract C85-033856.
Patents Abstracts of Japan–Unexamined Applications Sect. P, Section No. 367; vol. 9, No. 151, PO 136.
Bogomolov: Chemical Abstracts 74:71034c (1971).
Bogomolov: Chemical Abstracts 81:20366z (1974).
Vogelzang: Chemical Abstracts 102:28400d (1985).

*Primary Examiner*—Robert J. Warden
*Assistant Examiner*—Robert Benson
*Attorney, Agent, or Firm*—Foley & Lardner

[57] ABSTRACT

A method is disclosed for detecting the occurrence of a binding or complex-forming reaction between specific substances by utilizing the binding reaction to complete an electrical circuit, and then measuring a change in the electrical state of this circuit. In a preferred embodiment, a layer of antigen is coated onto a non-conductive base between a pair of electrically conductive layers superposed on the base. Antibodies which react with the foregoing antigen are treated so that they become bound to fine electrically conductive, metallic particles. The electrically conductive particles having antibody bound thereto are then added to the antigen layer deposited on the base and allowed to react therewith. Electrically conductive particles are thereby bound to the base due to the binding reaction between the antigen and antibody to thereby form aggregates of electrically conductive particles which bridge the electrically conductive layers and complete the circuit. Such a method is highly useful for the detection of antigens in the blood serum of a human patient.

19 Claims, 3 Drawing Sheets

METHOD FOR ELECTRONIC DETECTION OF A BINDING REACTION

This invention was made with government support under a small business innovation research grant awarded by the National Institute of General Medical Sciences. The government has certain rights in the invention.

FIELD OF THE INVENTION

This invention relates to a new method or electronically detecting a binding reaction between a pair of chemical substances, particularly biogenic substances such as antigens and antibodies. The present invention further provides a new method for electronic immunoassay.

BACKGROUND OF THE INVENTION

It is a well known principle of immunology that living organisms produce microscopic substances called antibodies to defend the body against invading foreign substances or microorganisms, such as bacteria and viruses. Antibodies typically act to neutralize microscopic foreign substances by binding to them and destroying them or rendering them harmless. Antibodies and globulin proteins of the blood plasma and are often referred to as gamma globulins.

When a foreign substance such as a bacterium or virus enters a human or animal body, production of antibodies to combat the infection is stimulated by the presence of one or more antigens. Antigens related to invading organisms comprise a foreign substance that comes from the invading organism, such as a piece of bacterium or virus. More generally, an antigen is any substance capable of triggering an immune response. Certain specialized cells of the body contact an antigen and produce antibodies specifically designed for that antigen. When released in the body, such antibodies identify and bind to the antigen, thereby combating the infection. Antibodies are highly specific and will generally bind only to the antigen which stimulated their creation.

When a person has been infected with certain diseases, that person's blood will often contain measurable levels of antigen specific to that disease. To determine whether such an infection is present, an immunodiagnostic test is performed using a sample of the patient's blood. The sample is mixed with a solution known to contain antibody specific to a certain disease or condition. If an antigen-antibody reaction occurs, the test result is positive, and the antigen is detected. Such a test is typically reversible, i.e., a solution or reagent known to contain a certain antigen can be used to determine whether or not the corresponding antibody is present in a sample. However, the antigen-antibody reaction occurs on a microscopic level and is not readily observable. Thus, all known immunodiagnostic tests provide some type of means for indicating that the antigen-antibody reaction has occurred.

A variety of techniques have been used to detect antigen-antibody reactions. The principal techniques presently in use are enzyme immunoassay, immunofluorescence, and radioimmunoassay. In typical enzyme immunoassay procedures, the antigen-antibody reaction is detected by the formation, by an enzyme, of a colored product from a colorless substrate. Immunofluorescence techniques indicate that a reaction has occurred by emission of small quantities of light which must generally be observed microscopically. Radioimmunoassay utilizes radioactive labeling substances so that occurrence of the antigen-antibody reaction is measured by the presence or absence of small amounts of radioactivity. These known methods are reliable but are slow and tedious.

Recently several types of electrical immunoassay techniques have been developed. Such methods utilize an electronic endpoint for measuring immune reactions. As used herein, "electronic endpoint" means a change in electrical properties which indicates that a binding reaction has occurred, such as a change in current, voltage, or resistance as a result of the antigen-antibody reaction.

One such technique utilizes field effect transistors coated with a layer of antibody in the gate region. If an antigen-antibody reaction occurs, the charge concentration of the transistor changes. Examples of this type of system are given in Schneck U.S. Pat. No. 4,238,757, issued Dec. 9, 1980; Guckel U.S. Pat. No. 4,180,771, issued Dec. 25, 1981; and Malmros U.S. Pat. No. 4,334,880, issued June 15, 1982.

Several other methods have been proposed for measuring immunologic reactions electrically. A voltammetric immunoassay can be carried by labeling one immunoreactant with an electroactive substance. Pace U.S. Pat No. 4,233,144, issued Nov. 11, 1980, is illustrative of one such technique. Another method involves sandwiching an antigen-antibody layer between two conductive layers and measuring the electrical capacitance of the resulting laminate. Giaever U.S. Pat. No. 4,054,646, issued Oct. 18, 1977, described such a method. A further method combines change effect signal detection with an enzyme immunoassay technique. Such a method is disclosed by Gibbons U.S. Pat. No. 4,287,300, issued Sept. 1, 1981. The foregoing electrical methods have, however, failed to provide medical practitioners and laboratories with a simple, fast, sensitive, inexpensive and easy-to-use method of performing an immunodiagnostic test.

One aspect of the present invention involves the use of antigen or antibody-labelled colloidal gold particles. In general, "colloidal gold" refers to a suspension of fine gold particles in water or aqueous solution, which gold particles have a particular antibody bound to the outer surfaces thereof. Preparation of such particles is disclosed by DeMey, et al. U.S. Pat. No. 4,446,238, issued May 1, 1984, and DeMey, et al. U.S. Pat. No. 4,420,558, issued Dec. 13, 1983. The entire contents of both such DeMey patents are incorporated herein by reference. Such collodial gold preparations have been previously used in immunodiagnostic tests wherein the results are determined optically by observing small amounts of light reflected as a result of the antigenantibody reaction. The foregoing patents to DeMey disclose a bright field light method of the foregoing type. The present invention advantageously employs colloidal gold in a new immunodiagnostic method utilizing an electronic endpoint.

SUMMARY OF THE INVENTION

The present invention provides an advantageous method for detecting a binding reaction between a pair of first and second substances, particularly biogenic substances, which bind together to form a chemical complex. The method of the invention involves bringing the substances together so that the binding reaction between them causes completion (closing) of an open electrical circuit. The resulting change in the electrical state of the circuit indicates the binding reaction.

According to a further aspect of the invention, a diagnostic element for use in detecting a binding reaction comprises a pair of spaced-apart, electrical conductors, particularly conductive layers, disposed side-by-side on a non-electrically conductive base. The space between these conductors can define a narrow channel. One of a pair of substances which bind to each other is deposited on and affixed to the surface of the non-conductive base between the conductors, e.g., on the bottom wall of the channel. Means forming an electrical circuit can be connected to each of the electrically conductive layers so that the channel constitutes a break in the circuit. As used herein, the term "diagnostic element" refers to the base, conductors, and layer of one of the binding substances, without the means defining the electrical circuit. Such a diagnostic element and means forming an electrical circuit can readily be used in conjunction with any suitable means for bridging the break in the circuit due to the binding reaction between the pair of substances. One such means involves adhering one of the substances to the surfaces of electrically conductive particles, as described in detail below.

According to another aspect of the invention, the foregoing method for detecting a reaction between complexforming substances is specifically applied to detection of an antigen-antibody reaction. The degree of aggregate formation, and the resulting electrical change, can be used to determine whether a patient sample contains a given antibody or antigen, as will be described in detail below.

BRIEF DESCRIPTION OF THE DRAWING

Preferred exemplary embodiments will hereafter be described in conjunction with the appended drawing, wherein like designations denote like elements, and.

DETAILED DESCRIPTION OF PREFERRED EXEMPLARY EMBODIMENTS OF THE INVENTION

The method of the present invention is particularly useful for detecting antigens in the body of a living creature. Such antigens includes drugs, toxins, hormones, allergens, tumor markers, factors, enzymes, steroids, nucleotides and other substances as listed in Huang U.S. Pat. No. 4,327,073, issued Apr. 27, 1982, the entire content of which is incorporated herein by reference. Any of the foregoing listed substances can provoke the production of a reactive substance (antibody) which reacts with and binds to the antigen. Accordingly, the method of the present invention is useful for detection of a wide variety of substances which may be present in the living body of a human or lower animal.

In particular, the method of the invention is especially useful in drug overdose treatment, where it is desired to quickly determine which drug a patient has taken. The method of the invention is also highly useful for detecting the presence of an antigen in the patient's bloodstream associated with a particular disease or condition.

FIGS. 1A–1E schematically illustrate a procedure for detecting an antigen according to the present invention. Referring to FIGS. 1A through 1C, a patient sample 11A (FIG. 1A) such as whole blood, blood serum or urine, containing a particular antigen 12A is mixed with a colloidal gold preparation 13A (FIG. 1B) containing a predetermined amount of gold particles 14A having antibodies 15A fixed to the outer surfaces thereof. Antibodies 15A specifically bind to antigen 12A (FIG. 1C). In the resulting mixture 16A, antigen 12A binds with available antibodies 15A, resulting in free complexes 18A, comprising both antigen 12A and antibody 15A bound to particles 14A. Since there are more antibodies 15A than antigens 12A, some antibodies 15A remain free, i.e., unbound to an antigen 12A.

An illustrated in FIGS. 2A–2C, the foregoing procedure is also carried out using a control sample 11B (FIG. 2A) lacking the antigen 12A and a second colloidal gold preparation 13B (FIG. 2B) substantially identical in composition to preparation 13A used with patient sample 11A. The thus-formed second mixture 16B (FIG. 2C) lacks the complexes 18A shown in FIG. 1A, and correspondingly has a greater number of particles 14B having unbound antigen 15B on the surfaces thereof. The first mixture 16A, corresponding to the patient sample (FIG. 1C), and the second mixture 16B (FIG. 2C), corresponding to the control, are then ready for use with a reaction detector 20 according to the invention (FIGS. 1D, 2D).

Figure 3:
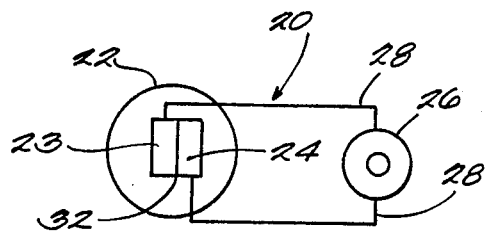
FIG. 3 is a schematic diagram illustrating a reaction detector according to one embodiment of the invention.

Referring now to FIG. 3, reaction detector 20 includes a non-electrically conductive base 22, a pair of thin, spaced-apart electrically conductive layers 23, 24 disposed side-by-side on base 22 with a channel 32 formed therebetween, and means defining an electrical circuit, such as an ohmmeter 26 functionally connected to layers 23, 24 as shown by means such as wires 28. Base 22 is typically made of a non-conductive material, such as polystyrene, glass or crystalline silicon. Layers 23, 24 may be formed of any conductive material, particularly an electrically conductive metal such as, for example, gold, silver, copper, chromium or aluminum.

Figures 1, 2:
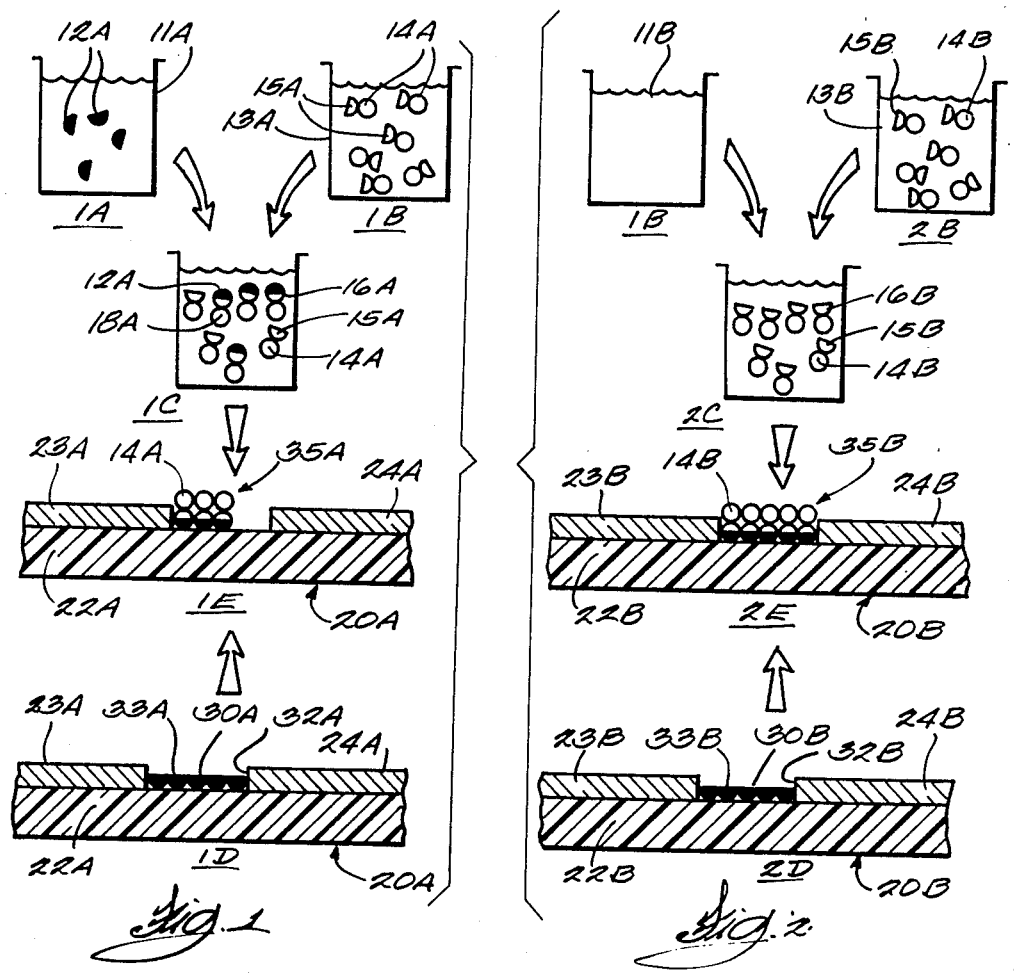
FIGS. 1A, 1B, 1C, 1D and 1E and FIGS. 2A, 2B, 2C, 2D and 2E are schematic diagrams illustrating an immunodiagnostic method according to the invention.

Referring again to FIGS. 1 and 2, identical first and second reaction detectors 20A (FIG. 1D) and 20B (FIG. 2D) are prepared in advance for use with mixtures 16A, 16B, respectively. Samples of antigen in a carrier liquid (e.g., water or saline solution) are poured into shallow channels or grooves 32A, 32B defined between layers 23A,B and 24A,B under conditions effective to cause antigen to bind to the surfaces of bottom walls 33A,B of channels 32A,B to form antigen layers 30A, 30B (FIG. 1D, 2D). These antigen layers 30A, 30B are made of the same type of antigen as antigen 12A to be detected.

Referring now to FIG. 1E, first mixture 16A (FIG. 1C), corresponding to patient sample 11A (FIG. 1A), is poured into channel 32A of first detector 20A under conditions effective to cause binding of antigen layer 30A and antibody 15A. The foregoing procedure is also carried out using the control mixture 16B (lacking complexes 18A) and second detector 20B (FIG. 2E).

Conductive particles 14A having free antibodies 15A thereon effectively become bound to bottom wall 33A via antigen layer 30A due to the antigen-antibody binding reaction. The reaction conditions employed to incubate the antigen-antibody reaction are well known. Complexes 18A containing antigen 12A from sample 11A do not tend to become bound to bottom wall 33A. After a suitable time to allow the antigen-antibody interaction to take place, channel 32A may, if desired, be flushed with a suitable liquid, e.g., water or saline solution, to wash away any unbound particles 14A, then dried by any suitable means, such as heating or allowing the reaction detector to stand open to the air.

Figure 4A:
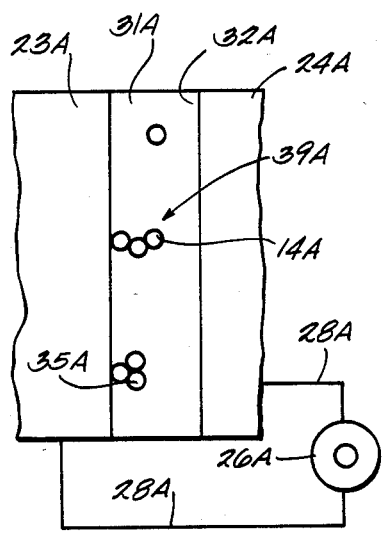
FIGS. 4A and 4B are schematic diagrams showing aggregate formation according to the method of FIGS. 1A–1E and 2A–2E, respectively.
Figure 4B:
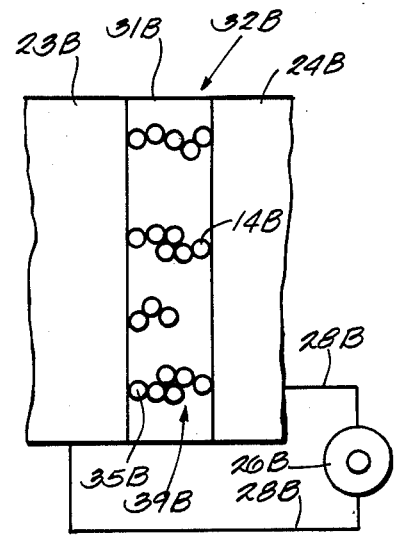

Referring now to FIGS. 4A and 4B, FIG. 4A corresponds to the same state as FIG. 1E, and FIG. 4B corresponds to the same state as FIG. 2E. FIGS. 4A, 4B illustrate the differences in the extent of the binding reaction not apparent in FIGS. 1E, 2E. Ohmmeters 26A and 26B register the resistance across channels 32A and 32B for each of the detectors 20A and 20B. For the control (FIG. 4B), all particles 14B having free antibodies 15B deposited thereon are available for binding with antigen layer 30B bound to bottom wall 33B. As a result, complexes 35B are formed at bottom wall 33B and are anchored thereto. As illustrated in FIG. 4B, complexes 35B tend to cluster together in contact with each other to form aggregates or chains 39B which effectively bridge channel 32B. Since particles 14B are electrically conductive, aggregates 39B effectively provide an electrical connection between layers 23B and 24B, completing an electrical circuit defined by ohmmeter 26B, wires 28B, layers 23B, 24B, and aggregates 39B. This is reflected by the resistance reading given by ohmmeter 26B. A drastic decrease in resistance occurs as a result of bridging of aggregates 39B.

The reaction for the mixture 16A corresponding to the patient sample proceeds in a similar fashion, except that this mixture 16A already contains complexes 18A formed by reaction of antigen 12A with antibody 15A. Since the antibodies of these complexes 18A are already bound with at least some antigen 12A, these complexes 18A do not tend to bind to the layer of antigen 30A at bottom wall 33A. In mixture 16A, the number of free antibodies 15A deposited on particles 14A is less than in mixture 16B, since some of these antibodies 15A were used to form complexes 18A. As shown in FIG. 4A, aggregates 39A form, but there are fewer such aggregates, and correspondingly less bridging of channel 32A. As a result, the decrease in resistance registered by ohmmeter 26A is less than the decrease in resistance registered by ohmmeter 26B. This difference in readings indicates the presence of antigen 12A in the patient sample 11A. If patient sample 11A does not contain any antigen 12A, then the decrease in resistance for reaction detector 20A would be the same as the decrease in resistance for detector 20B.

If resistance values corresponding to specific antigen levels in the sample are well known for a specific test, the foregoing procedure can be carried out without the control illustrated in FIGS. 2A–2E, 4B. However, the use of a control is preferred because the comparative resistance reading produced by the control afford more accurate results.

Figure 5:
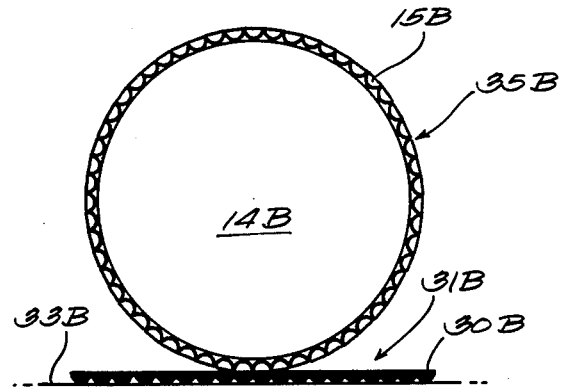
FIG. 5 is a schematic diagram showing binding of a conductive particle to a non-conductive base according to one embodiment of the invention.

The procedure shown in FIGS. 1 through 4 is greatly simplified for purposes of illustration. Conductive particles 14A,B are larger than antigen 12A and antibodies 15A,B. A number of antibodies 15A,B are bound to a single conductive particle 14A or 14B, and similarly a number of antigens 12A can bind with antibodies 15A on the surface of a single particle 14A or 14B. FIG. 5 schematically illustrates how a conductive particle 14B having antibodies 15B on its surface becomes bound to bottom wall 33B via antigen layer 30B.

Complexes 18A as referred to above may in fact comprise particles 14A having some free antibodies 15A on the surfaces thereof and some antibodies 15A bound to antigens 12A. In these complexes 18A, however, the proportion of free antibodies (unbound to antigen 12A in mixture 16A) is low enough so that the complex 18A will not subsequently bind to bottom wall 33A of channel 32A.

The reaction detector 20 used in the foregoing procedure is specifically designed as follows. The width of channel 32 may vary, particularly in relation to the simple numerical average diameter of the conductive particles forming a chain to bridge channel 32. The following table states preferred ranges for dimensions according to the present invention:

| Average Conductive Particle Diameter (Microns) | Channel Width (Microns) | Ratio of Channel Width to Particle Diameter |
|---|---|---|
| 0.01–500 | 0.1–20,000 | 5:1 to 40:1 |
| 0.01–10 | 0.1–100 | 10:1 to 30:1 |
| 0.01–1 | 1–25 | 15:1 to 25:1 |

A 20:1 ratio of channel width to average particle diameter is typical, e.g., the channel has a width of 10 microns, and the average diameter of the conductive particles is 0.5 microns.

As is known, antigens have an affinity for polystyrene and tend to become bound thereto under certain conditions. Antibodies by contrast readily become bound to the surfaces of fine metal particles, such as gold particles, using the procedure described below. Thus, in embodiments of the invention which involve antigen-antibody binding, it is preferred to bind the antigen to the bottom wall of the channel and bind the antibodies to the conductive particles. However, the reverse arrangement (antigen-particles, antibody-channel) can also be employed.

Layers 23, 24 may have any desired dimensions which prove functional. These layers 23, 24 are preferably as thin as possible, and preferably have a thickness no greater than about 0.5 microns, particularly a thickness in the range of 0.001–0.005 microns. Conventional sputter deposition can be readily used to form layers 23, 24. Layers 23, 24 may have any desired shape, such as rectangular (per FIG. 2) or semicircular so as to define a circular "dot" on the non-conductive base. Generally, base 22 is made of plastic, preferably methyl cellulose, nylon or polystyrene. Base 22 is most preferably made of polystyrene of the type used to make microscope slides, since the polarity of antigen molecules causes such molecules to bind to the base to form a substantially complete, homogenous coating of antigen.

Glass by itself is not generally employed as base 22 since antigens have a poor affinity for a glass surface and it has proved difficult to adhere a layer of antigen to a glass slide. However, according to a further aspect of the invention, it has been found that a glass slide can be surface treated so that antigen affinity for the coating on the glass slide becomes about as great as antigen affinity for a polystyrene slide. This surface treatment comprises coating the glass slide with a thin layer of titanium oxynitride ($TiO_xN_y$). An example of this technique appears below.

Figure 8:
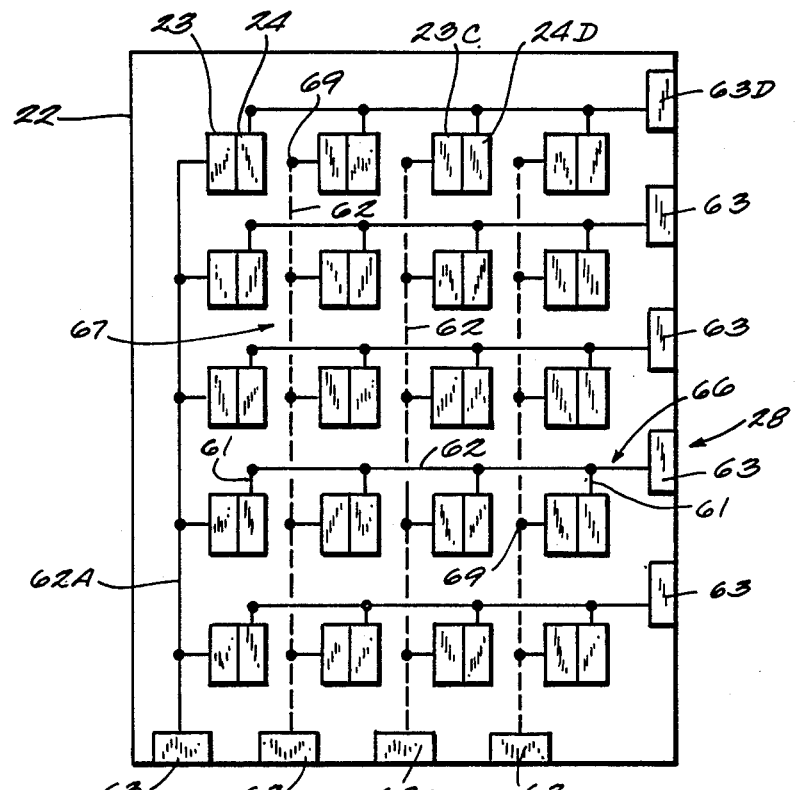
FIG. 8 is a schematic diagram of a multiple diagnostic element according to the invention.

FIG. 8 illustrates a further embodiment of the diagnostic element of the invention wherein a multiplicity of layers 23, 24 are disposed on a single non-conductive base 22. Conductive means 28 for this embodiment comprises a series of individual electrical conductors 61 which each connect to a common conductor 62 which in turn connects to a terminal plate 63 mounted on the edge of base 22. Pairs of layers 23, 24 are arrayed in rows and columns on base 22.

In the embodiment of FIG. 8 rows of plates 63 are disposed on adjacent sides of rectangular base 22. To prevent overlapping between a first set 66 of conductors 62 connected to layers 23 and a second set 67 of conductors 62 connected to layers 24, all but one of conductors 62 of second set 67 are located on the reverse side of base 22. These conductors 62 are illustrated by broken lines in FIG. 8. Outer conductor 62A does not cross any conductors 62 of first set 66 and thus does not need to be on the other side of base 22, although it can be so located if desired. Individual conductors 61 connected to common conductors 62 of second set 67 on the reverse side of base 22 include portions 69 which extend through the thickness of base 22 and connect with such conductors 62 (shown by broken lines in FIG. 7).

Ohmmeter 26 can be connected to various combinations of terminal plates 63 to measure resistance for each pair of layers 23, 24. To make such a measurement, ohmmeter 26 is connected to two plates 63 on different edges of base 22. In the embodiment of FIG. 8, connecting an ohmmeter to plates 63C, 63D would test the indicated pair of layers 23C, 24D.

The foregoing embodiment allows a single diagnostic element according to the invention to test a single patient sample for a number of different substances, such as antigens, since each pair of layers 23, 24 can have a different substance bound therebetween, or have no substance bound therebetween so as to provide a control, as described above.

EXAMPLE

The following procedure was used to make a suspension of gold particles labeled with antibodies according to the present invention. About 1 ml (milliliter) of a 1% w/v (weight/volume) solution of gold chloride in water were mixed with about 0.1 ml of Kodal D-19 photographic developer (containing a weak acid) to reduce the gold chloride to form gold particles. The resulting mixture was washed with distilled water by centrifugation at about 15,000 g to obtain a suspension of pure gold particles in water.

Goat anti-rabbit IgG antibodies were added to a pH 9.6 carbonate buffer to form an aqueous 1:5,000 (w/v) antibody solution. 1.0 ml of this solution was added to the gold particles, and the resulting mixture was allowed to set overnight at room temperature. The gold particles from this mixture, bound with the goat anti-rabbit IgG, were washed by centrifugation at about 15,000 g with phosphate buffered saline to remove excess antibody.

Figure 6:
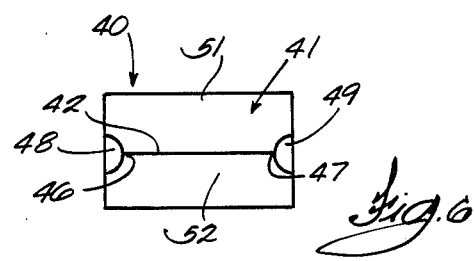
FIG. 6 is a schematic diagram of a diagnostic element according to one embodiment of the invention.
Figure 7:
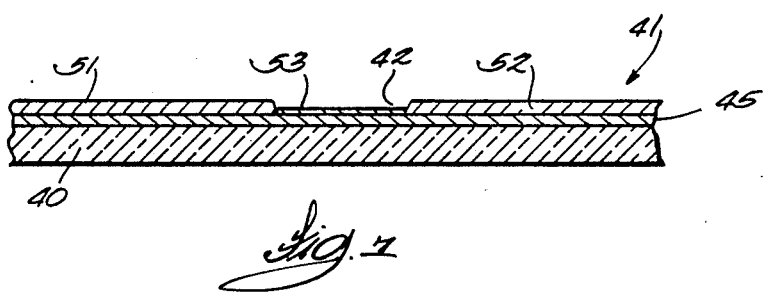
FIG. 7 is a cross-sectional view of the diagnostic element of FIG. 6.

Referring now to FIGS. 6 and 7, glass microscope slides 40 were coated with a thin layer 45 of titanium oxynitride ($TiO_xN_y$). Titanium oxynitride films of varying composition were deposited onto the glass slides by radio-frequency (rf) magnetron sputter deposition. The instrument used to deposit the titanium oxynitride coating was a Materials Research Corporation Model 822 Sputtersphere. A titanium target was used as the cathode. The system base pressure was $3 \times 10^{-7}$ Torr. The system was backfilled with a mixture of nitrogen and oxygen. Sputtering occurred at a total pressure of $8 \times 10^{-3}$ Torr. The forward power was 1,500 W, the target voltage was 314 V, reflected power was 0 watts, cathode to anode distance was $2\frac{1}{2}$ inches and the sputtering time was 30 minutes.

The oxynitridge materials were formed by reactive deposition in an oxygen/nitrogen plasma. The ratio of oxygen to nitrogen was varied to change the film composition. The composition of the film was then determined with Auger electron spectroscopy. A nitrogen to oxygen molar ratio of 0.30 to 0.40 yielded a film having superior antigen adherence. The amount of antigen adherence on the $TiO_xN_y$ films was comparable to that on plastic slides and was on order of magnitude larger than antigen adherence to uncoated glass under similar conditions.

A gold-palladium alloy (60:40) was then evaporated onto the upper surface of each slide 40 to form an evenly distributed gold-palladium layer 41 having a thickness of 1,000 angstroms on each slide 40. A scratch (line) 42 was then made in the surface of each gold-palladium layer 41 between points 46, 47 using a sharp needle.

A blunt instrument was used to rub away layer 41 in areas 48, 49. The result left a pair of 1,000 angstrom thick conductive layers 51, 52 separated by non-conductive line 42. An ohmmeter reading on areas 51, 52 (across line 42) gave a reading of greater than 2 million ohms.

An aqueous rabbit IGG solution was placed along the entire length of line 42 and incubated for 18 hours (overnight) to form an antigen layer 53. The IGG solution was then removed and the slides 40 were rinsed with phosphate buffered saline solution. The previously prepared colloidal suspension of gold-tagged anti-rabbit-IGG (gold particle diameters 0.1–0.5 mm) was then applied to line 42.

Formation of gold aggregates was then observed microscopically. Aggregates as large as about 20 microns long were observed, and groups of adjoining aggregates were also noted. Generally, aggregate size varied from about 1 to 20 microns in length. In one embodiment, formation of a large aggregate spanning a scratch (line 42) having a width of about 5 microns was observed. No complete bridging was observed for lines 42 on slides 40 which exceeded 20 microns in width. However, such larger line width are likely to be useful if other experimental conditions are adjusted accordingly, e.g. larger diameter gold particles are employed. In some cases imperfections in the point of the needle used to form lines 42 by scratching gave rise to several parallel lines 42. This should be avoided, since aggregate bridging of all of the parallel lines would likely be required to produce a substantial change in resistance when an ohmmeter is connected to layers 51, 52.

A a control slide was processed in the same manner as slides 40 except that the control slide was not treated with rabbit IGG solution. Only a few small aggregates remained on this slide segment after rinsing with phosphate buffered saline solution.

An ohmmeter was connected across layers 51, 52 for various test slides. For one slide 40, the resistance reading decreased to about 64,000 ohms from more than 2 million ohms. Little or no resistance changes were noted for most slides 40 wherein line 42 was excessively wide or multiple lines 42 were formed due to needle-point imperfections.

It will be understood that the above description is of preferred exemplary embodiments of the present invention, and the invention is not limited to the specific forms shown. Modifications may be made in the design and arrangement of the elements without departing from the scope of the present invention as expressed in the appended claims.

What is claimed is:

1. A method of detecting, in a sample, a first one of a pair of first and second substances, which substances specifically bind together to form a complex, said method comprising: mixing said sample with electrically conductive particles under conditions effective to cause binding of said first substance, if present in said sample, to the surface of said particles;

contacting said electrically conductive particles with a layer of said second substance which substantially spans a bottom wall of a channel between a pair of side-by-side, spaced-apart electrical conductors superposed on a substantially non-electrically conductive base, each of said conductors being connected to means defining an electrical circuit which includes said conductors and said channel therein, the binding reaction between said first and second substances causing said particles to be bound to said bottom wall to form electrically conductive aggregates;

removing unbound particles; and measuring a change in the electrical current flow through said circuit caused by formation of said aggregates in said channel, in the widthwise direction thereof, said width being the distance between said conductors, said electrical change indicating the presence of said first substance in said sample.

2. The method of claim 1, wherein said electrically conductive particles consist essentially of at least one metal selected from the group consisting of silver and gold.

3. The method of claim 2, wherein said particles have an average diameter in the range of from 0.01 to 1.0 microns.

4. The method of claim 1, wherein said pair of substances comprises an antibody and one member selected from the group consisting of microorganisms hormones, allergens, tumor markers, enzymes, steroids, and nucleotides.

5. The method of claim 1, wherein said step of measuring a change in current flow further comprises measuring a change in the electrical resistance across said electrical circuit.

6. The method of claim 1, wherein said channel has a width in the range of about 0.1 to 100 microns.

7. The method of claim 5, further comprising the step of operatively connecting an ohmmeter to said conductors to form said electrical circuit.

8. A method of detecting a substance in a test sample, which substance is one of a pair of substances that undergo a specific binding reaction with each other, comprising the steps of:

(1) mixing, in a liquid medium, electrically conductive particles, said particles having a first one of said pair of substances bound to the surfaces thereof, with said test sample containing an unknown quantity of the second of said pair of substances, under conditions effective to cause binding of said second substance in said test sample to said first substance on the surfaces of said particles;

(2) disposing said particles on a substantially continuous layer of said second substance bound to an essentially non-conductive base to form aggregates of said particles bound to said layer of said second substance, said layer of said second substance substantially spanning the width of a channel between a pair of side-by-side, spaced apart conductive layers superposed on said non-conductive base, each of said conductive layers being connected to means defining an electrical circuit including said conductive layers and said channel;

(3) removing excess unbound electrically conductive particles from said layer of said second substance; and (4) measuring a change in current flow through said circuit caused by the presence of said aggregates in said channel.

9. The method of claim 8, wherein said first substance is an antibody and said second substance is an antigen.

10. The method of claim 8, wherein said step (3) further comprise flushing said layer of said second substance to remove said unbound particles, and then drying said layer of said second substance having said aggregates bound thereto.

11. The method of claim 9, wherein said step (1) further comprises mixing said test sample with a preparation of colloidal electrically conductive metal particles having said antibodies bound to the surfaces thereof.

12. The method of claim 8, further comprising a step (5) of comparing said change with a standard value which corresponds to a value determined by performing steps (1) through (4) on a sample free of said second substance.

13. A diagnostic element, comprising
    a substantially non-electrically conductive base;
    a plurality of pairs of conductors, said pairs disposed on said base in spaced-apart positions, said conductors of said pairs being superposed side-by-side on said base and spaced-apart to define a channel therebetween, each of said channels having a width in the range of about 0.1 to 100 microns, said width being the distance between said conductors of each of said pairs; a plurality of layers of different substances, each of which undergoes a specific binding reaction with another substance, each one of said layers being bound to said base in a different one of said channels and substantially spanning the width of each channel;
    a plurality of electrically conductive terminals disposed on said base; and
    electrical connection means for conducting an electrical current from each one of said pairs of said conductors to a corresponding pair of said terminals, one of each pair of terminals being electrically connected to one conductor of the associated pair of conductors, and the other of each pair of terminals being electrically connected to the other conductor of said pair of conductors.

14. The diagnostic element of claim 13, wherein said terminals are disposed proximate an edge of said base.

15. The diagnostic element of claim 13, wherein said electrically conductive layers consist essentially of a conductive metal and have thicknesses no greater than about 0.5 microns.

16. The diagnostic element of claim 13, wherein said base comprises a layer of titanium oxynitride formed on a glass support.

17. The diagnostic element of claim 13, wherein said layers of said substances consist essentially of antigens.

18. The diagnostic element of claim 13, wherein said layers of said substances are each selected from the group consisting of microorganisms, hormones, allergens, tumor markers, enzymes, steroids, and nucleotides.

19. The element of claim 13, wherein said base is substantially rectangular, said terminals are disposed in a pair of row along two adjacent edges of said base, and each of said pairs of conductors are associated with a different pair of said terminals such that no two conductors of a pair are connected by said electrical connection means to the same two terminals as the conductors of any other pair.

* * * * *